United States Patent
Katoh et al.

(10) Patent No.: US 9,884,095 B2
(45) Date of Patent: Feb. 6, 2018

(54) MILK-DERIVED BASIC PROTEIN FRACTION AS SKIN SENSITIVITY IMPROVING AGENT

(71) Applicant: MEGMILK SNOW BRAND CO., LTD., Hokkaido (JP)

(72) Inventors: Ken Katoh, Hokkaido (JP); Noriko Ueda, Hokkaido (JP); Hiroshi Ueno, Hokkaido (JP); Yuko Ono, Hokkaido (JP); Norimichi Nakahata, Miyagi (JP); Takahiro Moriya, Miyagi (JP); Daisaku Kobayashi, Shizuoka (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

(21) Appl. No.: 14/850,485

(22) Filed: Sep. 10, 2015

(65) Prior Publication Data

US 2015/0374797 A1 Dec. 31, 2015

Related U.S. Application Data

(62) Division of application No. 13/981,698, filed as application No. PCT/JP2012/050617 on Jan. 13, 2012, now abandoned.

(30) Foreign Application Priority Data

Jan. 26, 2011 (JP) ................. 2011-014441

(51) Int. Cl.
*A61K 38/44* (2006.01)
*A61K 38/01* (2006.01)
*A61K 8/64* (2006.01)
*A61Q 19/00* (2006.01)
*A23L 2/66* (2006.01)
*C07K 14/47* (2006.01)
*C12N 9/08* (2006.01)
*A61K 38/17* (2006.01)
*A61K 38/40* (2006.01)
*A61K 38/54* (2006.01)
*A23K 20/147* (2016.01)
*A23K 20/142* (2016.01)
*A23K 50/40* (2016.01)
*A23L 33/19* (2016.01)

(52) U.S. Cl.
CPC ............ *A61K 38/44* (2013.01); *A23K 20/142* (2016.05); *A23K 20/147* (2016.05); *A23K 50/40* (2016.05); *A23L 2/66* (2013.01); *A23L 33/19* (2016.08); *A61K 8/64* (2013.01); *A61K 38/018* (2013.01); *A61K 38/1709* (2013.01); *A61K 38/40* (2013.01); *A61K 38/54* (2013.01); *A61Q 19/00* (2013.01); *C07K 14/47* (2013.01); *C12N 9/0065* (2013.01); *C12Y 304/21001* (2013.01); *C12Y 304/21004* (2013.01); *C12Y 304/23002* (2013.01); *A23V 2002/00* (2013.01); *A61K 2800/10* (2013.01); *A61K 2800/85* (2013.01); *C12Y 111/01007* (2013.01)

(58) Field of Classification Search
CPC .................................................... A61K 38/018
See application file for complete search history.

(56) References Cited

U.S. PATENT DOCUMENTS

| | | |
|---|---|---|
| 5,068,224 A | 11/1991 | Fryklund et al. |
| 5,420,112 A | 5/1995 | Lewis et al. |
| 5,633,228 A | 5/1997 | Lewis et al. |
| 5,756,686 A | 5/1998 | Heldin et al. |
| 5,866,418 A | 2/1999 | Ballard et al. |
| 5,932,259 A | 8/1999 | Kato et al. |
| 6,506,727 B1 | 1/2003 | Hansson et al. |
| 8,404,644 B2 | 3/2013 | Johnson et al. |
| 8,420,599 B2 | 4/2013 | Serizawa et al. |
| 2004/0081673 A1 | 4/2004 | Rayner et al. |
| 2004/0214750 A1 | 10/2004 | Georgiades |

(Continued)

FOREIGN PATENT DOCUMENTS

| | | |
|---|---|---|
| EP | 0 308 386 | 3/1989 |
| EP | 0704218 | 4/1996 |

(Continued)

OTHER PUBLICATIONS

Van Leeuwen et al. J. Anim. Physiol. a. Anim. Nutr. 2000, 83:15-23.*

(Continued)

*Primary Examiner* — Bin Shen
(74) *Attorney, Agent, or Firm* — Greenblum & Bernstein, P.L.C.

(57) ABSTRACT

A skin sensitivity improving agent which is safe and, when routinely taken or applied to the skin, exerts an effect of improving deterioration in peripheral sensation is provided. The present invention also provides a food, a drink, a feed or a cosmetic for improving sensation which exerts an effect of improving deterioration in peripheral sensation when orally taken or applied to the skin. The skin sensitivity improving agent includes, as the active ingredient, a basic protein fraction derived from milk or a degraded basic protein fraction derived from milk. By orally taking the basic protein fraction derived from milk or the degraded basic protein fraction derived from milk or applying the same directly to the skin, deterioration in sensation, in particular, peripheral sensation can be improved. Thus, a food, a drink, a feed or a cosmetic for improving sensation can be obtained.

9 Claims, No Drawings

(56) References Cited

U.S. PATENT DOCUMENTS

| | | |
|---|---|---|
| 2009/0270309 A1 | 10/2009 | Cornish et al. |
| 2010/0210531 A1 | 8/2010 | Johnson et al. |
| 2010/0216709 A1 | 8/2010 | Scheule et al. |
| 2010/0234296 A1 | 9/2010 | Serizawa et al. |
| 2013/0225497 A1 | 8/2013 | Kato et al. |
| 2013/0225501 A1 | 8/2013 | Kato et al. |
| 2015/0064158 A1 | 3/2015 | Katoh et al. |

FOREIGN PATENT DOCUMENTS

| | | |
|---|---|---|
| EP | 1228708 | 8/2002 |
| EP | 2208734 | 7/2010 |
| EP | 2764870 | 8/2014 |
| JP | 2-288897 | 11/1990 |
| JP | 05-32557 | 2/1993 |
| JP | 7-501340 | 2/1995 |
| JP | 7-507799 | 8/1995 |
| JP | 8-151331 | 6/1996 |
| JP | 2003-89629 | 3/2003 |
| JP | 2003-146883 | 5/2003 |
| JP | 2003-204785 | 7/2003 |
| JP | 2004-502788 | 1/2004 |
| JP | 2007-246413 | 9/2007 |
| JP | 2008-214265 | 9/2008 |
| JP | 2009-514804 | 4/2009 |
| JP | 2010-538020 | 12/2010 |
| WO | 92/00994 | 1/1992 |
| WO | 02/05828 | 1/2002 |
| WO | 2004/024180 | 3/2004 |
| WO | 2009/137880 | 11/2009 |

OTHER PUBLICATIONS

Martinez-Gomis et al. Archives of Oral Biology, 1999, 44:901-906.*

Elagamy et al., Int. Dairy J. 1996, 6:129-145.

Fee et al., Separation and Purification Technology, 2006, 48:143-149.

Tomita et al., "Potent antibacterial peptides generated by pepsin digestion of bovine lactoferrin", J Diary Sci., 1991, 74:4137-4142.

Shin et al., "Identification of lactoperoxidase in mature human milk", J. Nutr. Biochem, 2000, 11:94-102.

Taiwanese Office Action issued in TW Patent Appl. No. 101102016, dated Oct. 26, 2015.

Japanese Office Action issued in JP Patent Appl. No. 2012-554720, dated Oct. 21, 2015.

Extended European Search Report issued in EP Patent Appl. No. 12739663.8, dated Oct. 8, 2015.

Pouliot et al., "Milk Growth Factors as Health Products: Some Technological Aspects", International Dairy Journal, vol. 16, No. 11, pp. 1415-1420, 2006.

Apel et al., "Effect of Locally Delivered IGF-1 on Nerve Regeneration During Aging: An Experimental Study in Rats", Muscle & Nerve, vol. 41, No. 3, pp. 335-341, 2010.

Rabinovsky, "The Multifunctional Role of IGF-1 in Peripheral Nerve Regeneration", Neurological Research, vol. 26, No. 2, pp. 204-210, 2004.

Nakahata et al., "Studies on Expression Mechanism of Physiological Functions of Ceramides Having Skin Protection Function", Annual Report of Cosmetology, vol. 10, pp. 1-2, 2002.

International Search Report for PCT/JP2012/050617, dated Mar. 13, 2012.

International Preliminary Report on Patentability for PCT/JP2012/050617, dated Aug. 8, 2013.

U.S. Appl. No. 13/982,012 to Hiroshi Ueno et al., filed Jul. 26, 2013.

Manni et al., "Cholecystokinin-8 enhances nerve growth factor synthesis and promotes recovery of capsaicin-induced sensory deficit" Brit. J. Pharm. 129:744-750, 2000.

Terada et al., Modern Medicine, vol. 30, p. 63(2477)-72(2486), 1998.

Database WPI, Week 200353, Thomson Scientific, London, GB; AN 2003-561912, XP002744841 (Mar. 28, 2003), Abstract.

Australian Office Action issued in AU Patent Application No. 2012210013, dated Oct. 14, 2016.

* cited by examiner

US 9,884,095 B2

MILK-DERIVED BASIC PROTEIN FRACTION AS SKIN SENSITIVITY IMPROVING AGENT

CROSS-REFERENCE TO RELATED APPLICATIONS

This application is a Divisional of U.S. patent application Ser. No. 13/981,698, (abandoned), which is a National Stage of International Application No. PCT/JP2012/050617, filed Jan. 13, 2012, which claims priority to Japanese Patent Application No. 2011-014441, filed Jan. 26, 2011. The disclosures of each of U.S. patent application Ser. No. 13/981,698 and PCT/JP2012/050617 are expressly incorporated by reference herein in their entireties.

TECHNICAL FIELD

The invention relates to a skin sensitivity improving agent that includes a basic protein fraction or a degraded basic protein fraction as an active ingredient and improves deterioration in peripheral sensation, and a skin sensitivity improving food, drink, feed, or cosmetic that includes the skin sensitivity improving agent.

BACKGROUND ART

In recent years, an increase in age-related diseases such as osteoporosis, dementia and the like has become a serious social issue along with aging of population. Various drugs have been developed to prevent or improve such age-related diseases. However, since drugs always need to take side effects into consideration, in recent years, attempts have been made to prevent or improve age-related diseases through a change in eating habits or intake of a specific food ingredient. For example, it is known that osteoporosis is prevented or improved by intake of a basic protein contained in cow milk (see Patent Document 1). A dementia therapeutic agent that prevents or improves Alzheimer-type dementia and contains sphingomyelin which is one of the phospholipids containing relatively abundantly in cow milk as an active ingredient has also been known (see Patent Document 2).

Deterioration in peripheral sensation can be known as one of the age-related symptoms. The deterioration in peripheral sensation also occurs due to not only aging, but also diseases such as diabetes and the like. Deterioration in peripheral sensation may occur following troubles; for example, as it can't feel hot immediately when touching a hot object, a risk of burns or the like increases or the discovery of an injury becomes delay due to deterioration in pain sensation. In recent year, in order to decrease such a risk, studies that improve deterioration in peripheral sensation due to ageing or diseases have been conducted. For example, it has been reported that sphingomyelinase or phosphatidylcholine-specific phospholipase C, which are enzymes that increase biosynthesis of endogenous ceramides promote differentiation of PC-12 cells which is one of the neural cell lines through the secretion of neurotrophic factors from Swiss 3T3 fibroblast cells (see Non-patent Document 1). However, since ceramides and the above enzymes are not food ingredients, it is necessary to take account of safety. Therefore, a safe agent that is effective to improve deterioration in peripheral sensation through daily intake or skin application has been desired.

PRIOR ART DOCUMENT

Patent Document

Patent Document 1: JP-A-H08-151331
Patent Document 2: JP-A-2003-146883

Non-Patent Document

Non-patent Document 1: Norimichi Nakahata and Satoko Okubo, Studies on Expression Mechanism of Physiological Functions of Ceramides Having Skin Protection Function, Annual Report of Cosmetology, Vol. 10, 2002

SUMMARY OF THE INVENTION

Problems to be Solved by the Invention

An object of the present invention is to provide a safe and skin sensitivity improving agent that is effective to improve deterioration in peripheral sensation through daily intake or skin application. Another object of the present invention is to provide a sensation-improving food, drink, feed, or cosmetic that is effective to improve deterioration in peripheral sensation through oral intake or skin application.

Means for Solving the Problems

The inventors of the invention, in consideration of those problems, searched for a safe component that exhibits an excellent improvement effect to the deterioration in sensation. As a result, the inventors found that deterioration in sensation, particularly peripheral sensation, can be improved by oral intake or skin application of a basic protein fraction derived from milk (hereinafter referred to as "milk-derived basic protein fraction") or a degraded basic protein fraction obtained by degrading the milk-derived basic protein fraction using a protease (hereinafter referred to as "degraded milk-derived basic protein fraction"). The inventors thus completed a skin sensitivity improving agent by utilizing the milk-derived basic protein fraction and/or the degraded milk-derived basic protein fraction as an active ingredient. The inventors also found that a skin sensitivity improving food, drink, feed, or cosmetic can be obtained by adding the skin sensitivity improving agent to a food, drink, feed, or the like, respectively. These findings have led to completion of the invention.

Specifically, the invention provides the following.

(1) A skin sensitivity improving agent including a milk-derived basic protein fraction as an active ingredient.

(2) The skin sensitivity improving agent according to (1), wherein the milk-derived basic protein fraction contains basic amino acids in an amount of 15 wt % or more based on total amino acids.

(3) The skin sensitivity improving agent according to (1) or (2), wherein the milk-derived basic protein fraction is obtained by bringing milk or a milk-derived raw material into contact with a cation-exchange resin to allow basic proteins to be adhered on the cation-exchange resin, and eluting the fraction adhered on the cation-exchange resin using an eluant having a sodium chloride concentration of 0.1 to 1.0 M.

(4) A skin sensitivity improving agent including a degraded milk-derived basic protein fraction as an active ingredient, the degraded milk-derived basic protein fraction being obtained by treating the milk-derived basic protein fraction according to any one of (1) to (3) with a protease.

(5) The skin sensitivity improving agent according to (4), wherein the protease is at least one protease selected from the group consisting of pepsin, trypsin, chymotrypsin, and pancreatin.

(6) A skin sensitivity improving food, drink, feed, or cosmetic including the milk-derived basic protein fraction or the degraded milk-derived basic protein fraction according to any one of (1) to (5).

(7) A method for improving sensation of a mammal including administering a composition that includes a milk-derived basic protein fraction to the mammal via oral administration or application on skin.

(8) The method according to (7), wherein the milk-derived basic protein fraction contains basic amino acids in an amount of 15 wt % or more based on total amino acids.

(9) The method according to (7) or (8), wherein the milk-derived basic protein fraction is obtained by bringing milk or a milk-derived raw material into contact with a cation-exchange resin to allow basic proteins to be adhered on the cation-exchange resin, and eluting the fraction adhered on the cation-exchange resin using an eluant having a sodium chloride concentration of 0.1 to 1.0 M.

(10) A method for improving sensation of a mammal including administering a composition that includes a degraded milk-derived basic protein fraction to the mammal via oral administration or application on skin, the degraded milk-derived basic protein fraction being obtained by treating the milk-derived basic protein fraction according to any one of (7) to (9) with a protease.

(11) The method according to (10), wherein the protease is at least one protease selected from the group consisting of pepsin, trypsin, chymotrypsin, and pancreatin.

Effects of the Invention

The invention can thus provide a skin sensitivity improving agent that includes a milk-derived basic protein fraction or a degraded milk-derived basic protein fraction as an active ingredient, and a skin sensitivity improving food, drink, feed, or cosmetic that includes a milk-derived basic protein fraction or a degraded milk-derived basic protein fraction. The skin sensitivity improving agent according to the invention exhibits an effect that improves deterioration in peripheral sensation.

EMBODIMENTS FOR CARRYING OUT THE INVENTION

The invention is characterized in that a milk-derived basic protein fraction or a degraded milk-derived basic protein fraction are used as active ingredients. The milk-derived basic protein fraction is obtained from mammalian milk such as cow milk, human milk, goat milk, or ewe milk, and the degraded milk-derived basic protein fraction is obtained by treating the milk-derived basic protein fraction with a protease. The milk-derived basic protein fraction has the following properties.

1) The milk-derived basic protein fraction comprises several types of proteins having a molecular weight of 3,000 to 80,000 determined by sodium dodecyl sulfate polyacrylamide gel electrophoresis (SDS-PAGE).

2) The milk-derived basic protein fraction includes proteins in an amount of 95 wt % or more, and includes a small amount of fats and ash.

3) The milk-derived basic protein fraction mainly includes lactoferrin and lactoperoxidase as proteins.

4) The milk-derived basic protein fraction has basic amino acids, such as lysine, histidine, arginine and the like in an amount of 15 wt % or more based on the total amino acids.

The basic protein fraction may be obtained by applying a milk-derived raw material, such as skim milk, whey or the like to a cation-exchange resin to adhered the basic proteins like on the cation-exchange resin, eluting the basic protein fraction adhered on the cation-exchange resin by using an eluant having a sodium chloride concentration of 0.1 to 1 M, collecting the eluted fraction, which is desalted and concentrated by using a reverse osmosis (RO) membrane, electrodialysis (ED), or the like, and optionally drying the resulting product, for example.

The following methods have been known as a method of obtaining a milk-derived basic protein fraction; a method of obtaining the fraction by contacting milk or a milk-derived raw material with a cation exchanger to adhere on the cation exchanger, and eluting the basic protein fraction adhered on the cation exchanger using an eluant having a pH of more than 5 and an ionic strength of more than 0.5 (JP-A-5-202098), a method of obtaining the fraction using an alginic acid gel (JP-A-61-246198), a method of obtaining the fraction from whey using porous inorganic particles (JP-A-1-86839), a method of obtaining the fraction from milk using a sulfated ester compound (JP-A-63-255300), or the like. A basic protein fraction obtained by such a method may be used in the invention. The degraded milk-derived basic protein fraction has the same amino acid composition as that of the milk-derived basic protein fraction. For example, the degraded milk-derived basic protein fraction may be obtained as a peptide composition having an average molecular weight of 4,000 or less by treating a milk-derived basic protein fraction obtained by the above methods with a protease such as pepsin, trypsin, or chymotrypsin, and optionally treating the resulting product with a protease such as pancreatin or the like.

The milk-derived basic protein fraction or the degraded milk-derived basic protein fraction may be used directly as the skin sensitivity improving agent according to the invention. Note that the skin sensitivity improving agent may be further mixed a raw material or the like that is normally used for drugs, food, drink, and feed, such as saccharides, lipids, proteins, vitamins, minerals, or flavors, or the like, in addition to the milk-derived basic protein fraction or the degraded milk-derived basic protein fraction, and the skin sensitivity improving agent may be prepared into a powdered drug, granules, a tablet, a capsule, a drinkable preparation, or the like by a conventional method. The skin sensitivity improving agent may also be used in common application form such as emulsion, cream, lotion, massage mask, or the like. The skin sensitivity improving agent in preparation form may be prepared by a conventional method while appropriately adding the milk-derived basic protein fraction or the degraded milk-derived basic protein fraction used as an active ingredient in the invention, and may be used as a cosmetic. Another component, e.g., ceramide, sphingomyelinase, or sphingomyelin or the like that exhibits a skin sensitivity improving effect may be used in combination with the milk-derived basic protein fraction or the degraded milk-derived basic protein fraction. In the experiments described later using mice, the peripheral sensation was improved by orally administering the milk-derived basic protein fraction or the degraded milk-derived basic protein fraction in an amount of 10 mg/kg weight or more, and preferably 20 mg/kg weight or more per mouse. Therefore, deterioration in sensation, particularly peripheral sensation, is expected to be improved when an adult generally takes the milk-derived basic protein fraction or the degraded milk-derived basic protein fraction in an amount of 10 mg/day or more, and preferably 20 mg/day or more, and thus it is desired to take the above necessary quantity. When applying the milk-derived basic protein fraction or the degraded milk-derived basic protein fraction to skin, the skin liniment may contain the milk-derived basic protein fraction or the degraded milk-derived basic protein fraction in an amount of 0.001 to 40 wt %, and preferably 0.1 to 10 wt %, based on the total amount of the skin liniment.

A skin sensitivity improving food or drink according to the invention may be produced by mixing the milk-derived basic protein fraction or the degraded milk-derived basic protein fraction to a normal food or drink, such as yogurt, milk-based drink, wafer, dessert or the like. It is preferable that the skin sensitivity improving food or drink contain the milk-derived basic protein fraction or the degraded milk-derived basic protein fraction in an amount of 0.5 to 2000 mg per 100 g of the food or drink so that an adult can take the milk-derived basic protein fraction or the degraded milk-derived basic protein fraction in an amount of 10 mg/day or more, although the content of the milk-derived basic protein fraction or the degraded milk-derived basic protein fraction is appropriately determined depending on the type of the food or drink. A skin sensitivity improving feed according to the invention may be produced by adding the milk-derived basic protein fraction or the degraded milk-derived basic protein fraction to a normal feed, such as livestock feed, pet food or the like. It is preferable that the skin sensitivity improving feed contain the milk-derived basic protein fraction or the degraded milk-derived basic protein fraction in an amount of 0.5 to 2000 mg per 100 g of the feed so that the milk-derived basic protein fraction or the degraded milk-derived basic protein fraction is taken in an amount of 10 mg/day or more.

The method of mixing the milk-derived basic protein fraction or the degraded milk-derived basic protein fraction may not be particularly limited. For example, the milk-derived basic protein fraction or the degraded milk-derived basic protein fraction is suspended or dissolved in deionized water, and the mixture is stirred and prepared in the form of a drug, food, drink, or feed. The stirring/mixing conditions are not particularly limited as long as the milk-derived basic protein fraction or the degraded milk-derived basic protein fraction is uniformly mixed. The mixture may be stirred/mixed using an ultra-disperser, a TK-homomixer, or the like. The solution containing the composition may optionally be concentrated using an RO membrane, or freeze-dried so that the solution can be easily used for a drug, food, drink, or feed. A sterilization treatment conventionally used in the production of a drug, food, drink, or feed may be employed in the invention. Dry-heat sterilization may also be employed for a powdery product. Therefore, it is possible to produce drugs, food, drink, and feed in various forms (e.g., liquid, gel, powder, or granules) that contain the milk-derived basic protein fraction or the degraded milk-derived basic protein fraction of the invention.

The invention is further described below by way of examples and test examples. Note that the following examples are for illustrative purposes only, and should not be construed as limiting the invention.

Example 1

A column (diameter: 5 cm, height: 30 cm) filled with 400 g of sulfonated Chitopearl (cation-exchange resin; manufactured by Fuji Spinning Co., Ltd.) was sufficiently washed with deionized water. 40 l (liters) of unsterilized skim milk (pH 6.7) was passed through the column at a flow rate of 25 ml/min. The column was then sufficiently washed with deionized water, and a basic protein fraction adhered on the resin was eluted with a 0.02 M carbonate buffer solution (pH 7.0) containing 0.98 M sodium chloride. The eluate was desalted and concentrated using a reverse osmosis (RO) membrane, and freeze-dried to obtain 21 g of powdery milk-derived basic protein fraction (Example product 1). The molecular weight of the milk-derived basic protein fraction determined by sodium dodecyl sulfate polyacrylamide gel electrophoresis (SDS-PAGE) was distributed in the range of 3000 to 80,000. The milk-derived basic protein fraction had the composition shown in Table 1. The milk-derived basic protein fraction was hydrolyzed using 6 N hydrochloric acid at 110° C. for 24 hours, and the amino acid composition of the milk-derived basic protein fraction was analyzed using an amino acid analyzer ("L-8500" manufactured by Hitachi Ltd.). The results are shown in Table 2. The protein composition of the milk-derived basic protein fraction was analyzed by ELISA. As shown in Table 3, the milk-derived basic protein fraction had a lactoferrin content and a lactoperoxidase content of 40% or more. The basic protein fraction may be used directly as the skin sensitivity improving agent according to the invention.

TABLE 1

| Water | 1.06 (wt %) |
|---|---|
| Protein | 96.50 |
| Fat | 0.56 |
| Ash | 0.27 |
| Others | 1.61 |

TABLE 2

| Aspartic acid | 10.1 (wt %) |
|---|---|
| Serine | 5.3 |
| Glutamic acid | 12.3 |
| Proline | 4.7 |
| Alanine | 5.7 |
| Leucine | 10.2 |
| Lysine | 8.4 |
| Histidine | 2.5 |
| Arginine | 7.2 |
| Others | 33.6 |

TABLE 3

| Lactoferrin | 42.5 (wt %) |
|---|---|
| Lactoperoxidase | 45.6 |
| Insulin-like growth factor 1 | 0.005 |
| Others | 11.895 |

Example 2

A column (diameter: 100 cm, height: 10 cm) filled with 30 kg of cation-exchange resin (SP Toyopearl; manufactured by Tosoh Corporation) was sufficiently washed with deionized water. 3 t of cheese whey (pH 6.2) that had been heat-sterilized at 121° C. for 30 seconds was passed through the column at a flow rate of 10 l/min. The column was then sufficiently washed with deionized water, and a basic protein fraction adhered on the resin was eluted with a 0.1 M citrate buffer solution (pH 5.7) containing 0.9 M sodium chloride. The eluate was desalted and concentrated by electrodialysis (ED), and freeze-dried to obtain 183 g of a powdery milk-derived basic protein fraction (Example product 2). The milk-derived basic protein fraction thus obtained may be used directly as the skin sensitivity improving agent according to the invention.

Example 3

50 g of the milk-derived basic protein fraction obtained in Example 1 was dissolved in 10 l of distilled water. After the addition of 1% pancreatin (manufactured by Sigma), the mixture was reacted at 37° C. for 2 hours. After completion of the reaction, the protease was inactivated by heating the mixture at 80° C. for 10 minutes to obtain 48.3 g of a degraded milk-derived basic protein fraction (Example product 3). The degraded milk-derived basic protein fraction thus obtained may be used directly as the skin sensitivity improving agent according to the invention.

Test Example 1

(Study on Cell Differentiation-Promoting Activity)
Swiss 3T3 cells, which is one of the fibroblast cell lines known to be present in skin, were cultured for 2 days under the condition that Example product 1 of the milk-derived basic protein fraction or Example product 3 of the degraded milk-derived basic protein fraction was added at a concentration of 0.03 to 1%, respectively (Example product 1: group A, Example product 3: group B). As a control, Swiss 3T3 cells were cultured for 2 days without adding Example product 1 of the milk-derived basic protein fraction or Example product 3 of the degraded milk-derived basic protein fraction (group C). PC-12 cells, which is one of the neural cell lines, were cultured adding the culture medium of Swiss 3T3 cells, and morphological differentiation of the PC-12 cells was observed.

As the results, PC-12 cells were highly differentiated when adding the culture mediums of the group A or B. The above experiment was repeated several times, and the differentiation ratio was determined using an optical microscope. It was confirmed that 95% or more of the cells were differentiated in both cases of group A and B. In contrast, PC-12 cells were not differentiated when adding the culture medium of the group C. No differentiation was observed using an optical microscope when the experiment was repeated several times. It was thus confirmed that the milk-derived basic protein fraction obtained in Example 1 and the degraded milk-derived basic protein fraction obtained in Example 3 promoted differentiation of PC-12 cells which is one of the neural cell lines.

Test Example 2

(Study on Skin Sensitivity Improving Effect Using Experimental Animals)
A skin sensitivity improving effect was evaluated by the hot plate test that is a thermal stimulation behavioristic approach developed by Woolfe and MacDonald. 24-week-old hairless mice (Hos:HR-1) were divided into three groups (10 mice/group). Example product 2 (milk-derived basic protein fraction) was orally administered to each mouse using a sonde in an amount of 0, 10, or 20 mg/kg weight once daily for 4 weeks. Each mouse was placed on a hot plate at 54° C., and the time elapsed until the mouse made an escape behavior such as taking off the foot from the hot plate, standing up, or jumping was measured. The maximum time of escape behavior positive reaction time that is time until the mouse made an escape behavior after applying thermal stimulation was set to 30 seconds. When the escape behavior positive reaction time was 30 seconds or more, the escape behavior positive reaction time was determined to be 30 seconds. The results are shown in Table 4.

TABLE 4

| Example product 2 | Escape behavior positive reaction time |
|---|---|
| 0 mg | 29.2 ± 0.14 sec |
| 10 mg | 22.2 ± 0.17 sec |
| 20 mg | 20.1 ± 0.25 sec |

As shown in Table 4, the escape behavior positive reaction time tended to be shortened when administering Example product 2 (milk-derived basic protein fraction) in an amount of 10 mg, and significantly shortened when administering Example product 2 (milk-derived basic protein fraction) in an amount of 20 mg. It was thus confirmed that deterioration in sensation, particularly peripheral sensation, can be prevented or improved by intake of Example product 2 (milk-derived basic protein fraction).

Test Example 3

(Study on Skin Sensitivity Improving Effect by Oral Intake)
Healthy elderly persons (average age: 75±3) who suffered deterioration in sensation in the hands were divided into following five groups (10 subjects/group).
Group A: the subjects did not take a milk-derived basic protein fraction or a milk-derived basic protein fraction,
Group B: the subjects took the milk-derived basic protein fraction obtained in Example 1 in an amount of 10 mg for 6 weeks,
Group C: the subjects took the milk-derived basic protein fraction obtained in Example 1 in an amount of 20 mg for 6 weeks,
Group D: the subjects took the degraded milk-derived basic protein fraction obtained in Example 3 in an amount of 10 mg for 6 weeks, and
Group E: the subjects took the degraded milk-derived basic protein fraction obtained in Example 3 in an amount of 20 mg for 6 weeks.
The pain sensation in the palm and the arch of the foot was measured with 4 criteria (normal, deterioration I, deterioration II, and deterioration III) before the intake and after the intake for 6 weeks with reference to the pain sensation in the medial side of the arm using a pain/touch-pressure sensation measuring device (Algesiometer; manufactured by Intercross Ltd.) in accordance with the instruction manual. A questionnaire survey on an improvement in sensation in the hands was carried out to each elderly person after the intake for 6 weeks. The results are shown in Tables 5 to 8.
(Measuring Method)
The pain sensation was evaluated using five pins having different thickness at five fulcrum positions. The thinnest pin 1 was rolled along the medial side of the arm, and the subject was asked about the degree of normal pain sensation.
The pin 1 was then rolled along the palm and the bottom of the foot while sequentially changing the holder fulcrum position to determine the fulcrum position at which the same pain sensation degree as the first pain sensation occurred.
(Evaluation Method)
The algesiometer is designed so that the pain sensation occurs to the same extent between when rolling the pin 1 (fulcrum: 50 g) along the medial side of the arm and when rolling the pin 2 (fulcrum: 50 g) along the palm. The pain sensation was evaluated as follows in accordance with the instruction manual. The pain sensation was evaluated by points, and the average points were calculated.
Normal (0 points): The same pain sensation occurred when rolling the pin 2 (fulcrum: 50 g).
Deterioration I (1 point): The same pain sensation occurred when rolling the pin 1 (fulcrum: 50 g).
Deterioration II (2 point): The same pain sensation occurred when rolling the pin 1 (fulcrum: 60 g).
Deterioration III (3 point): The same pain sensation occurred when rolling the pin 1 (fulcrum: 70 g).

TABLE 5

|  | Normal | Deterioration I | Deterioration II | Deterioration III | Average value |
|---|---|---|---|---|---|
| Hand sensation measurement (before intake) | | | | | |
| Group A | 0 | 2 | 3 | 5 | 2.3 |
| Group B | 0 | 1 | 5 | 4 | 2.3 |
| Group C | 0 | 1 | 5 | 4 | 2.3 |
| Group D | 0 | 1 | 4 | 5 | 2.4 |
| Group E | 0 | 1 | 5 | 4 | 2.3 |
| Hand sensation measurement (after intake for 6 weeks) | | | | | |
| Group A | 0 | 2 | 4 | 5 | 2.2 |
| Group B | 0 | 3 | 5 | 2 | 1.9 |
| Group C | 2 | 4 | 3 | 1 | 1.3 |
| Group D | 1 | 2 | 4 | 3 | 1.9 |
| Group E | 2 | 2 | 5 | 1 | 1.5 |

TABLE 6

|  | Normal | Deterioration I | Deterioration II | Deterioration III | Average value |
|---|---|---|---|---|---|
| Foot bottom sensation measurement (before intake) | | | | | |
| Group A | 0 | 2 | 3 | 5 | 2.3 |
| Group B | 0 | 1 | 4 | 5 | 2.4 |
| Group C | 0 | 1 | 3 | 6 | 2.5 |
| Group D | 0 | 1 | 6 | 3 | 2.2 |
| Group E | 0 | 1 | 4 | 5 | 2.4 |
| Foot bottom sensation measurement (after intake for 6 weeks) | | | | | |
| Group A | 0 | 2 | 3 | 5 | 2.3 |
| Group B | 1 | 4 | 1 | 4 | 1.8 |
| Group C | 2 | 3 | 3 | 2 | 1.5 |
| Group D | 0 | 3 | 6 | 1 | 1.8 |
| Group E | 1 | 3 | 5 | 1 | 1.6 |

TABLE 7

| Hand sensation | | | |
|---|---|---|---|
|  | Worsened | Unaltered | Improved |
| Group A | 2 | 7 | 1 |
| Group B | 1 | 5 | 4 |
| Group C | 0 | 2 | 8 |
| Group D | 0 | 3 | 7 |
| Group E | 0 | 2 | 8 |

TABLE 8

| Foot bottom sensation | | | |
|---|---|---|---|
|  | Worsened | Unaltered | Improved |
| Group A | 2 | 7 | 1 |
| Group B | 0 | 6 | 4 |
| Group C | 0 | 2 | 8 |
| Group D | 0 | 5 | 5 |
| Group E | 0 | 2 | 8 |

As shown in Tables 5 to 8, the sensation in the palm and the bottom of the foot tended to be improved by intake of Example product 1 (milk-derived basic protein fraction) or Example product 3 (degraded milk-derived basic protein fraction) in an amount of 10 mg, and was significantly improved by intake of Example product 1 (milk-derived basic protein fraction) or Example product 3 (degraded milk-derived basic protein fraction) in an amount of 20 mg. Deterioration in sensation, particularly in peripheral sensation, is expected to be improved when an adult takes the milk-derived basic protein fraction or the degraded milk-derived basic protein fraction in an amount of 10 mg/day or more generally, and preferably 20 mg/day or more.

Example 4

(Preparation of Skin Sensitivity Improving Cosmetic (Cream))

A skin sensitivity improving cosmetic (cream) was prepared by mixing the degraded milk-derived basic protein fraction (Example product 3) obtained in Example 3 with the raw materials in the ratio shown in Table 9.

TABLE 9

| Glycerol monostearate (self-emulsifiable) | 10.0 |
|---|---|
| Purified lanolin | 6.0 |
| Liquid paraffin | 5.0 |
| Jojoba oil | 5.0 |
| Parabene | 0.3 |
| Degraded milk-derived basic protein fraction (Example production 3) | 1.0 |
| Essence | Proper quantity |
| Sterilized ion-exchanged water | Balance (total: 100) |

Test Example 4

(Study on Skin Sensitivity Improving Effect Via Skin Application)

Healthy elderly persons (average age: 75±3) who suffered deterioration in sensation in the hands were divided into groups A and B (15 subjects/group). The subjects of the group A were applied the cosmetic (cream) that was prepared in the same manner as Example product 4, but did not contain a skin sensitivity improving agent, once daily to whole of the hands and the feet thereof, and the subjects of the group B were applied the skin sensitivity improving cosmetic (cream) obtained in Example 4 once daily to whole of the hands and the feet thereof. The application period was 6 weeks. The pain sensation in the palm and the arch of the foot was measured by 4 criteria (normal, deterioration I, deterioration II, or deterioration III) before the application and after the application for 6 weeks with respect to the pain sensation in the medial side of the arm using a pain/touch-pressure sensation measuring device (Algesiometer; manufactured by Intercross Ltd.) in accordance with the instruction manual. After the completion of the application for 6 weeks, a questionnaire survey on an improvement in sensation in the hands was carried out to each subject. The results are shown in Tables 10 to 13. The measurement was performed in the same manner as in Test Example 3.

TABLE 10

|         | Normal | Deterioration I | Deterioration II | Deterioration III | Average value |
|---------|--------|-----------------|------------------|-------------------|---------------|
| Hand sensation measurement (before application) | | | | | |
| Group A | 0 | 4 | 6 | 5 | 2.1 |
| Group B | 0 | 5 | 4 | 6 | 2.1 |
| Hand sensation measurement (after application for 6 weeks) | | | | | |
| Group A | 1 | 3 | 7 | 4 | 1.9 |
| Group B | 3 | 6 | 3 | 3 | 1.4 |

TABLE 11

|         | Normal | Deterioration I | Deterioration II | Deterioration III | Average value |
|---------|--------|-----------------|------------------|-------------------|---------------|
| Foot bottom sensation measurement (before application) | | | | | |
| Group A | 0 | 5 | 5 | 5 | 2.0 |
| Group B | 0 | 5 | 6 | 4 | 1.9 |
| Foot bottom sensation measurement (after application for 6 weeks) | | | | | |
| Group A | 1 | 3 | 5 | 6 | 2.1 |
| Group B | 2 | 6 | 6 | 1 | 1.4 |

TABLE 12

| | Hand sensation | | |
|---|---|---|---|
| | Worsened | Unaltered | Improved |
| Group A | 2 | 12 | 1 |
| Group B | 1 | 6 | 9 |

TABLE 13

| | Foot bottom sensation | | |
|---|---|---|---|
| | Worsened | Unaltered | Improved |
| Group A | 3 | 13 | 1 |
| Group B | 0 | 9 | 5 |

As shown in Tables 10 to 13, the sensation in the palm and the bottom of the foot tended to be improved by applying the skin sensitivity improving cosmetic (cream) of Example product 4. It was thus confirmed that deterioration in sensation, particularly peripheral sensation, is expected to be improved by applying cream that includes the skin sensitivity improving agent according to the invention.

Example 5

(Preparation of Skin Sensitivity Improving Liquid Nutrient Composition)

5 g of Example product 1 (milk-derived basic protein fraction) was dissolved in 4995 g of deionized water. The solution was stirred by a TK-homomixer ("TK ROBO MICS" manufactured by PRIMIX Corporation) at 6000 rpm for 30 minutes to obtain a basic protein fraction solution having a basic protein fraction content of 100 mg/100 g. 4.0 kg of casein, 5.0 kg of a soybean protein, 1.0 kg of fish oil, 3.0 kg of perilla oil, 18.0 kg of dextrin, 6.0 kg of a mineral mixture, 1.95 kg of a vitamin mixture, 2.0 kg of an emulsifying agent, 4.0 kg of a stabilizer, and 0.05 kg of essence were added to 5.0 kg of the milk-derived basic protein fraction solution. A retort pouch (200 ml) was filled with the mixture. The mixture was then sterilized using a retort sterilizer (class-1 pressure vessel, "RCS-4CRTGN" manufactured by Hisaka Works, Ltd.) at 121° C. for 20 minutes to obtain 50 kg of a skin sensitivity improving liquid nutrient composition. The resulting skin sensitivity improving liquid nutrient composition was not observed any precipitation and the like, and did not exhibit abnormal flavor. The skin sensitivity improving liquid nutrient composition contained the milk-derived basic protein fraction in an amount of 10 mg/100 g.

Example 6

(Preparation of Skin Sensitivity Improving Gel-Like Food)

2 g of Example product 2 (milk-derived basic protein fraction) was dissolved in 708 g of deionized water. The solution was stirred using an ultra-disperser ("ULTRA-TURRAX T-25" manufactured by IKA Japan) at 9500 rpm for 30 minutes. 40 g sorbitol, 2 g of a sour agent, 2 g of essence, 5 g of pectin, 5 g of whey protein concentrate, 1 g of calcium lactate, and 235 g of deionized water were added to the solution. After stirring the mixture, the mixture was filled in a cheer pack (200 ml). After sterilizing the mixture at 85° C. for 20 minutes, the pack was tightly sealed, and thus five bags (Net 200 g each) of skin sensitivity improving gel-like food of the invention were prepared. The resulting skin sensitivity improving gel-like food was not observed any precipitation, and did not exhibit abnormal flavor. The skin sensitivity improving gel-like food contained the milk-derived basic protein fraction in an amount of 200 mg/100 g.

Example 7

(Preparation of Skin Sensitivity Improving Drink)

2 g of sour agent was dissolved in 706 g of deionized water, and 4 g of Example product 3 (degraded milk-derived basic protein fraction) was dissolved in the solution. The solution was stirred using an ultra-disperser ("ULTRA-TURRAX T-25" manufactured by IKA Japan) at 9500 rpm for 30 minutes. After the addition of 100 g of maltitol, 20 g of reduced starch syrup, 2 g of essence, and 166 g of deionized water, the resulting mixture was filled into a glass bottle (100 ml). After sterilizing the mixture at 95° C. for 15 seconds, the bottle was sealed to obtain ten bottles of skin sensitivity improving drink (100 ml/bottle). The resulting skin sensitivity improving drink was not observed any precipitation, and did not exhibit abnormal flavor. The skin sensitivity improving drink contained the degraded milk-derived basic protein fraction in an amount of 400 mg/100 g.

Example 8

(Preparation of Skin Sensitivity Improving Feed)

2 kg of Example product 3 (degraded milk-derived basic protein fraction) was dissolved in 98 kg of deionized water. The solution was stirred using a TK-homomixer ("MARK II 160" manufactured by PRIMIX Corporation) at 3600 rpm for 40 minutes to obtain a degraded milk-derived basic protein fraction solution containing the degraded milk-derived basic protein fraction in an amount of 2 g/100 g. 12 kg of soybean cake, 14 kg of skim milk powder, 4 kg of soybean oil, 2 kg of corn oil, 23.2 kg of palm oil, 14 kg of corn starch, 9 kg of flour, 2 kg of bran, 5 kg of a vitamin mixture, 2.8 kg of cellulose, and 2 kg of a mineral mixture were added to 10 kg of the degraded milk-derived basic protein fraction solution. The mixture was sterilized at 120° C. for 4 minutes to obtain 100 kg of skin sensitivity improving dog food. The skin sensitivity improving dog food contained the degraded milk-derived basic protein fraction in an amount of 200 mg/100 g.

Example 9

(Preparation of Skin Sensitivity Improving Agent (Tablet))

The raw materials were mixed in the ratio shown in Table 14. 1 g of the resulting mixture was formed and tableted by a conventional method to obtain a skin sensitivity improving agent of the invention. The skin sensitivity improving agent contained the milk-derived basic protein fraction in an amount of 100 mg/g.

TABLE 14

| | |
|---|---|
| Hydrated crystalline glucose | 83.5(wt %) |
| Milk-derived basic protein fraction (Example product 1) | 10.0 |
| Mineral mixture | 5.0 |
| Sugar ester | 1.0 |
| Essence | 0.5 |

Example 10

(Preparation of Skin Sensitivity Improving Cosmetic (Lotion))

A skin sensitivity improving cosmetic (lotion) was prepared by mixing the raw materials in the ratio shown in Table 15.

TABLE 15

| | |
|---|---|
| Sorbitol | 3.0 |
| Sodium DL-pyrrolidone carboxylate | 2.0 |
| Carboxymethyl cellulose | 0.3 |
| Parabene | 0.1 |
| Milk-derived basic protein fraction (Example product 2) | 1.5 |

TABLE 15-continued

| | |
|---|---|
| Essence | Proper quantity |
| Sterilized ion-exchanged water | Balance (total: 100) |

What is claimed is:

1. A method of improving skin sensitivity of a human subject suffering from deterioration of skin sensation, comprising:
   administering to the human subject an effective amount of a milk-derived basic protein fraction as an active ingredient to improve the skin sensitivity of the human subject, the milk-derived basic protein fraction comprising a lactoferrin content of 40 wt % or more and a lactoperoxidase content of 40 wt % or more.

2. The method according to claim 1, wherein the milk-derived basic protein fraction has basic amino acids in an amount of 15 wt % or more based on total amino acids.

3. The method according to claim 1, wherein the active ingredient is present in a food, drink, feed, or cosmetic.

4. The method according to claim 1, comprising administering the milk-derived basic protein fraction to skin of the subject.

5. The method according to claim 1, comprising administering the milk-derived basic protein fraction to a hand or foot of the subject.

6. A method of improving skin sensitivity of a human subject suffering from deterioration of skin sensation, comprising:
   administering to the human subject an effective amount of a degraded milk-derived basic protein fraction as an active ingredient to improve the skin sensitivity of the human subject, the degraded milk-derived basic protein fraction being a peptide composition having the same amino acid composition as that of a milk-derived basic protein fraction comprising a lactoferrin content of 40 wt % or more and a lactoperoxidase content of 40 wt % or more.

7. The method according to claim 6, wherein the active ingredient is present in a food, drink, feed, or cosmetic.

8. The method according to claim 6, comprising administering the degraded milk-derived basic protein fraction to skin of the subject.

9. The method according to claim 6, comprising administering the degraded milk-derived basic protein fraction to a hand or foot of the subject.

* * * * *